(12) United States Patent
Hofstetter et al.

(10) Patent No.: US 7,277,594 B2
(45) Date of Patent: Oct. 2, 2007

(54) SYSTEM AND METHOD FOR PREPARING AN IMAGE CORRECTED FOR THE PRESENCE OF A GRAVITY INDUCED DISTORTION

(75) Inventors: Robert Hofstetter, Bern (CH); Nicolas Guggenheim, Aesch (CH); José L. Scherrer, Oensingen (CH)

(73) Assignee: AO Technology AG, Chur (CH)

( * ) Notice: Subject to any disclaimer, the term of this patent is extended or adjusted under 35 U.S.C. 154(b) by 370 days.

(21) Appl. No.: 09/985,585

(22) Filed: Nov. 5, 2001

(65) Prior Publication Data

US 2002/0109705 A1    Aug. 15, 2002

Related U.S. Application Data

(63) Continuation of application No. PCT/CH99/00183, filed on May 3, 1999.

(51) Int. Cl.
G06K 9/40 (2006.01)
G06K 9/36 (2006.01)

(52) U.S. Cl. .................. 382/275; 382/289; 382/254

(58) Field of Classification Search .......... 382/100, 382/254, 276, 289, 293, 287, 275
See application file for complete search history.

(56) References Cited

U.S. PATENT DOCUMENTS

| | | | |
|---|---|---|---|
| 3,821,469 A | 6/1974 | Whetstone et al. | 178/18 |
| 3,983,474 A | 9/1976 | Kuipers | 324/43 |
| 4,058,114 A | 11/1977 | Soldner | 128/2 |
| 4,146,924 A | 3/1979 | Birk et al. | 364/513 |
| 4,182,312 A | 1/1980 | Mushabac | 433/68 |
| 4,204,225 A | 5/1980 | Mistretta | 358/111 |
| 4,209,254 A | 6/1980 | Reymond et al. | 356/152 |
| 4,262,306 A | 4/1981 | Renner | 358/93 |
| 4,341,220 A | 7/1982 | Perry | 128/630 |
| 4,358,856 A | 11/1982 | Stivender et al. | 378/167 |
| 4,396,945 A | 8/1983 | DiMatteo et al. | 358/107 |
| 4,418,422 A | 11/1983 | Richter et al. | 378/205 |
| 4,419,012 A | 12/1983 | Stephenson et al. | 356/141 |
| 4,437,161 A | 3/1984 | Anderson | 364/414 |
| 4,457,311 A | 7/1984 | Sorenson et al. | 128/660 |
| 4,465,069 A | 8/1984 | Barbier et al. | 128/303 |
| 4,473,074 A | 9/1984 | Vassiliadis | 128/303.1 |

(Continued)

FOREIGN PATENT DOCUMENTS

DE    195 06 197 A1    5/1996

(Continued)

OTHER PUBLICATIONS

Nolte et al., "Clinical Evaluation of a System for Precision Enhancement in Spine Surgery," *Clinical Biomechanics*, vol. 10, No. 6, pp. 293-303 (1995).

*Primary Examiner*—Matthew C. Bella
*Assistant Examiner*—Wes Tucker
(74) *Attorney, Agent, or Firm*—Jones Day

(57) ABSTRACT

The present invention relates to an imaging system for obtaining an image correctable for the presence of a gravity induced image error. The imaging system includes an imager to obtain an image of an object and a position measurement device to obtain position data indicative of a gravity-induced deformation of the imager. The position data may include gravity vector data indicative of an orientation of a gravity vector.

22 Claims, 3 Drawing Sheets

U.S. PATENT DOCUMENTS

| | | | |
|---|---|---|---|
| 4,485,815 A | 12/1984 | Amplatz et al. | 128/329 |
| 4,543,959 A | 10/1985 | Seponen | 128/653 |
| 4,571,834 A | 2/1986 | Fraser et al. | 33/1 |
| 4,583,538 A | 4/1986 | Onik et al. | 128/303 |
| 4,592,352 A | 6/1986 | Patil | 128/303 |
| 4,598,368 A | 7/1986 | Umemura | 364/414 |
| 4,602,622 A | 7/1986 | Bär et al. | 128/303 |
| 4,613,866 A | 9/1986 | Blood | 343/448 |
| 4,613,942 A | 9/1986 | Chen | 364/513 |
| 4,618,978 A | 10/1986 | Cosman | 378/164 |
| 4,638,798 A | 1/1987 | Shelden et al. | 128/303 |
| 4,649,504 A | 3/1987 | Krouglicof et al. | 364/559 |
| 4,651,732 A | 3/1987 | Frederick | 128/303 |
| 4,670,781 A | 6/1987 | Aubert et al. | 358/93 |
| 4,672,564 A | 6/1987 | Egli et al. | 364/559 |
| 4,674,057 A | 6/1987 | Caughman et al. | 364/513 |
| 4,729,098 A | 3/1988 | Cline et al. | 364/414 |
| 4,733,661 A | 3/1988 | Palestrant | 128/303 |
| 4,733,969 A | 3/1988 | Case et al. | 356/375 |
| 4,737,032 A | 4/1988 | Addleman et al. | 356/376 |
| 4,742,815 A | 5/1988 | Ninan et al. | 128/4 |
| 4,743,770 A | 5/1988 | Lee | 250/560 |
| 4,743,771 A | 5/1988 | Sacks et al. | 250/560 |
| 4,745,290 A | 5/1988 | Frankel et al. | 250/360 |
| 4,750,487 A | 6/1988 | Zanetti | 128/303 |
| 4,753,528 A | 6/1988 | Hines et al. | 356/1 |
| 4,760,851 A | 8/1988 | Fraser et al. | 128/774 |
| 4,761,072 A | 8/1988 | Pryor | 356/1 |
| 4,762,016 A | 8/1988 | Stoughton et al. | 74/479 |
| 4,763,652 A | 8/1988 | Brisson et al. | 128/328 |
| 4,764,016 A | 8/1988 | Johansson | 356/371 |
| 4,776,749 A | 10/1988 | Wanzenberg et al. | 414/680 |
| 4,779,212 A | 10/1988 | Levy | 364/562 |
| 4,782,239 A | 11/1988 | Hirose et al. | 250/561 |
| 4,791,934 A | 12/1988 | Brunnett | 128/653 |
| 4,793,355 A | 12/1988 | Crum et al. | 128/653 |
| 4,794,262 A | 12/1988 | Sato et al. | 250/560 |
| 4,803,976 A | 2/1989 | Frigg et al. | 128/92 |
| 4,821,200 A | 4/1989 | Öberg | 364/474.24 |
| 4,821,206 A | 4/1989 | Arora | 364/513 |
| 4,822,163 A | 4/1989 | Schmidt | 356/1 |
| 4,825,091 A | 4/1989 | Breyer et al. | 250/560 |
| 4,829,373 A | 5/1989 | Leberl et al. | 358/88 |
| 4,835,710 A | 5/1989 | Schnelle et al. | 364/513 |
| 4,836,778 A | 6/1989 | Baumrind et al. | 433/69 |
| 4,841,967 A | 6/1989 | Chang et al. | 128/303 |
| 4,869,247 A | 9/1989 | Howard, III et al. | 128/303.1 |
| 4,875,478 A | 10/1989 | Chen | 128/303 |
| 4,896,673 A | 1/1990 | Rose et al. | 128/660.03 |
| 4,907,252 A | 3/1990 | Aichinger et al. | 378/99 |
| 4,943,296 A | 7/1990 | Funakubo et al. | 606/166 |
| 4,945,914 A | 8/1990 | Allen | 128/653 |
| 4,955,891 A | 9/1990 | Carol | 606/130 |
| 4,970,666 A | 11/1990 | Welsh et al. | 364/522 |
| 4,987,488 A | 1/1991 | Berci | 358/93 |
| 4,991,579 A | 2/1991 | Allen | 128/653 |
| 5,016,639 A | 5/1991 | Allen | 128/653 |
| 5,027,818 A | 7/1991 | Bova et al. | 128/653 |
| 5,047,036 A | 9/1991 | Koutrouvelis | 606/130 |
| 5,050,608 A | 9/1991 | Watanabe et al. | 128/653 |
| 5,059,789 A | 10/1991 | Salcudean | 250/206.1 |
| 5,078,140 A | 1/1992 | Kwoh | 128/653.1 |
| 5,080,662 A | 1/1992 | Paul | 606/130 |
| 5,086,401 A | 2/1992 | Glassman et al. | 395/94 |
| 5,094,241 A | 3/1992 | Allen | 128/653.1 |
| 5,097,839 A | 3/1992 | Allen | 128/653.1 |
| 5,099,846 A | 3/1992 | Hardy | 128/653.1 |
| 5,107,839 A | 4/1992 | Houdek et al. | 128/653.1 |
| 5,119,817 A | 6/1992 | Allen | 128/653.1 |
| 5,142,930 A | 9/1992 | Allen et al. | 74/469 |
| 5,178,164 A | 1/1993 | Allen | 128/898 |
| 5,186,174 A | 2/1993 | Schlöndorff et al. | 128/653.1 |
| 5,197,476 A | 3/1993 | Nowacki et al. | 128/660.03 |
| 5,198,877 A | 3/1993 | Schulz | 356/375 |
| 5,207,223 A | 5/1993 | Adler | 128/653.1 |
| 5,211,164 A | 5/1993 | Allen | 128/653.1 |
| 5,211,165 A | 5/1993 | Dumoulin et al. | 128/653.1 |
| 5,230,338 A | 7/1993 | Allen et al. | 128/653 |
| 5,230,623 A | 7/1993 | Guthrie et al. | 433/72 |
| 5,249,581 A | 10/1993 | Horbal et al. | 128/664 |
| 5,251,127 A | 10/1993 | Raab | 364/413.13 |
| 5,257,998 A | 11/1993 | Ota et al. | 606/130 |
| 5,274,551 A | 12/1993 | Corby, Jr. | 364/413.13 |
| 5,278,756 A | 1/1994 | Lemchen et al. | 364/413.28 |
| 5,295,483 A | 3/1994 | Nowacki et al. | 128/660.03 |
| 5,299,288 A | 3/1994 | Glassman et al. | 395/80 |
| 5,300,080 A | 4/1994 | Clayman et al. | 606/130 |
| 5,305,203 A | 4/1994 | Raab | 364/413.13 |
| 5,309,913 A | 5/1994 | Kormos et al. | 128/653.1 |
| 5,325,855 A | 7/1994 | Daghighian et al. | 128/653.1 |
| 5,350,351 A | 9/1994 | Saffer | 601/2 |
| 5,383,454 A | 1/1995 | Bucholz | 128/653.1 |
| 5,389,101 A | 2/1995 | Heilbrun et al. | 606/130 |
| 5,394,457 A | 2/1995 | Leibinger et al. | 378/162 |
| 5,408,409 A | 4/1995 | Glassman et al. | 364/413.13 |
| 5,445,166 A | 8/1995 | Taylor | 128/897 |
| 5,479,597 A | 12/1995 | Fellous | 395/154 |
| 5,483,961 A | 1/1996 | Kelly et al. | 128/653.1 |
| 5,494,034 A | 2/1996 | Schlöndorff et al. | 128/653.1 |
| 5,517,990 A | 5/1996 | Kalfas et al. | 128/653.1 |
| 5,588,430 A | 12/1996 | Bova et al. | 128/653.1 |
| 5,617,857 A | 4/1997 | Chader et al. | 128/653.1 |
| 5,622,170 A | 4/1997 | Schulz | 128/653.1 |
| 5,630,431 A | 5/1997 | Taylor | 128/897 |
| 5,631,973 A | 5/1997 | Green | 382/128 |
| 5,662,111 A | 9/1997 | Cosman | 128/653.1 |
| 5,676,673 A | 10/1997 | Ferre et al. | 606/130 |
| 5,682,886 A | 11/1997 | Delp et al. | 128/653.1 |
| 5,711,299 A | 1/1998 | Manwaring et al. | 128/653.1 |
| 5,729,129 A | 3/1998 | Acker | 324/207.12 |
| 5,732,703 A | 3/1998 | Kalfas et al. | 128/653.2 |
| 5,735,278 A | 4/1998 | Hoult et al. | 128/653.2 |
| 5,748,767 A | 5/1998 | Raab | 382/128 |
| 5,755,725 A | 5/1998 | Druais | 606/130 |
| RE35,816 E | 6/1998 | Schulz | 356/376 |
| 5,769,078 A | 6/1998 | Kliegis | 128/653.1 |
| 5,769,789 A | 6/1998 | Wang et al. | 600/414 |
| 5,769,861 A | 6/1998 | Vilsmeier | 606/130 |
| 5,772,593 A | 6/1998 | Hakamata | 600/407 |
| 5,795,294 A | 8/1998 | Luber et al. | 600/407 |
| 5,799,099 A | 8/1998 | Wang et al. | 382/131 |
| 5,800,352 A | 9/1998 | Ferre et al. | 600/407 |
| 5,807,252 A | 9/1998 | Hassfeld et al. | 600/407 |
| 5,810,008 A | 9/1998 | Dekel et al. | 128/660.07 |
| 5,829,444 A | 11/1998 | Ferre et al. | 128/897 |
| 5,848,967 A | 12/1998 | Cosman | 600/426 |
| 5,880,976 A | 3/1999 | DiGioia III et al. | 364/578 |
| 5,995,738 A | 11/1999 | DiGioia, III et al. | 395/500.32 |
| 6,002,859 A | 12/1999 | DiGioia, III et al. | 395/500.32 |
| 6,021,343 A | 2/2000 | Foley et al. | 600/429 |
| 6,112,113 A | 8/2000 | Van Der Brug et al. | 600/427 |
| 6,120,465 A | 9/2000 | Guthrie et al. | 600/587 |
| 6,122,341 A | 9/2000 | Butler et al. | 378/20 |
| 6,135,946 A | 10/2000 | Konen et al. | 600/117 |
| 6,149,592 A | 11/2000 | Yanof et al. | 600/427 |
| 6,165,181 A | 12/2000 | Heilbrun et al. | 606/130 |
| 6,167,145 A | 12/2000 | Foley et al. | 382/128 |
| 6,167,295 A | 12/2000 | Cosman | 600/426 |
| 6,167,296 A | 12/2000 | Shahidi | 600/427 |
| 6,198,794 B1 | 3/2001 | Peshkin et al. | 378/42 |
| 6,205,411 B1 | 3/2001 | DiGioia, III et al. | 703/11 |
| 6,216,029 B1 | 4/2001 | Paltieli | 600/427 |
| 6,224,613 B1 | 5/2001 | Hofstetter | 606/130 |
| 6,226,548 B1 | 5/2001 | Foley et al. | 600/426 |

| | | | | | |
|---|---|---|---|---|---|
| 6,236,875 B1 | 5/2001 | Bucholz et al. ............ 600/407 | DE | 297 04 393 U1 | 7/1997 |
| 6,246,898 B1 | 6/2001 | Vesely et al. ............... 600/424 | EP | 0 062 941 A1 | 10/1982 |
| 6,256,529 B1 | 7/2001 | Holupka et al. ............ 600/427 | EP | 0 326 768 A2 | 8/1989 |
| 6,259,943 B1 | 7/2001 | Cosman et al. ............. 600/429 | EP | 0 591 712 A1 | 4/1994 |
| 6,275,725 B1 | 8/2001 | Cosman ...................... 600/426 | EP | 0 647 428 A2 | 4/1995 |
| 6,285,902 B1 * | 9/2001 | Kienzle et al. ............. 600/427 | EP | 0 832 609 A2 | 4/1998 |
| 6,298,262 B1 | 10/2001 | Franck et al. ............... 600/426 | GB | 2 094 590 A | 9/1982 |
| 6,332,891 B1 | 12/2001 | Himes ......................... 606/169 | WO | WO 90/05494 | 5/1990 |
| 6,341,231 B1 | 1/2002 | Ferre et al. ................. 600/424 | WO | WO 91/07726 | 5/1991 |
| 6,351,659 B1 | 2/2002 | Vilsmeier ................... 600/407 | WO | WO 94/23647 | 10/1994 |
| 6,351,662 B1 | 2/2002 | Franck et al. ............... 600/429 | WO | WO 94/24933 | 11/1994 |
| 6,739,752 B2 * | 5/2004 | Sabczynski et al. ........ 378/207 | WO | WO 95/15729 | 6/1995 |
| 2001/0007919 A1 | 7/2001 | Shahidi ....................... 600/427 | WO | WO 95/31148 | 11/1995 |
| 2001/0027271 A1 | 10/2001 | Franck et al. ............... 600/426 | WO | WO 96/11624 | 4/1996 |
| 2001/0039421 A1 | 11/2001 | Heilbrun et al. ............ 606/130 | WO | WO 97/29685 | 8/1997 |
| | | | WO | WO 97/29709 | 8/1997 |
| | FOREIGN PATENT DOCUMENTS | | WO | WO 97/47240 | 12/1997 |
| DE | 195 36 180 A1 6/1997 | | * cited by examiner | | |

SYSTEM AND METHOD FOR PREPARING AN IMAGE CORRECTED FOR THE PRESENCE OF A GRAVITY INDUCED DISTORTION

RELATED APPLICATIONS

This application is a continuation of National stage of application no. PCT/CH99/00183, May 3, 1999, which application is incorporated herein in its entirety.

FIELD OF THE INVENTION

The invention relates to a system and method for obtaining an image of an object. In particular, the invention relates to a system and method for obtaining an image corrected for the presence of a distortion caused by a gravity induced deformation of an imager used to obtain the image.

BACKGROUND OF THE INVENTION

The use of measuring instruments and imaging appliances often necessitates changes in the position or orientation of the measuring instrument depending on the type of measurement to be taken. For example, imagers or for obtaining x-ray images, such as the mobile or swivel-mounted x-ray imagers commonly used in surgery may be used to obtain images with the apparatus at different positions. Image intensifiers and c-arm appliances are examples of such imagers.

With imagers, such as x-ray apparatuses used in surgery, the orientation of the imager relative to the gravitational field of the Earth may have an influence, due to material deformations, on the measurement and, consequently, on the digitization of the image. With x-ray imagers using magneto-optical image digitization, the orientation of the apparatus relative to the Earth's magnetic field may also have a negative effect on the x-ray photographs (images). A further possible deformation of these x-ray images may be due to the influence of optical deformations occurring in the receiver, depending primarily on the composition of the radiation source and on the nature of the receiver, which may arise, for example, during the transformation of electrons into photons or during a subsequent transformation of the photons into an electrical signal.

A system for detecting the position and orientation of a surgical instrument or device within an object and for simultaneously displaying previously generated images corresponding to the detected position and orientation is disclosed in U.S. Pat. No. 5,383,454 to Buchholz. The Buchholz patent discloses that the tip of a probe can be moved to a defined position within the object with the location of the probe being observable on a single display screen, which simultaneously displays a previously generated image of the object. The position of the probe is determined by means of a three-dimensional sound digitizer.

SUMMARY OF THE INVENTION

One embodiment of the present invention relates to an imaging system for obtaining an image, which is correctable for the presence of a gravity induced image error. The system comprises an imager, such as an x-ray apparatus, to obtain an image of an object and a position measurement device to obtain position data indicative of a gravity-induced deformation of the imager. An example of a gravity induced image error is an error caused by a gravity induced mechanical deformation of the imager. The mechanical deformation may change, for example, the position of an imager source with respect to an imager receiver. Such deformations, as well as the resulting image error, may differ depending upon the orientation of the imager with respect to a gravity vector local to the imager. The present invention is preferably configured to obtain a correctable image for each orientation of the imager.

The position data may comprise image position data indicative of a position and orientation of the imager, for example, the position and orientation of the imager receiver with respect to the imager source. The imaging device preferably comprises markers having a known spatial relationship with respect to the imager and the position measurement device preferably comprises receivers to determine a respective position of the markers. The position data may also comprise, alone or in combination with the imager position data, gravity vector data indicative of an orientation of a gravity vector in which case the system preferably comprises at least one inclinometer for determining the orientation of the gravity vector. A processor of the imaging system is preferably configured to perform a coordinate transformation between the position and orientation of the imager and the gravity vector data to determine the position and orientation of the imager with respect to the gravity vector.

The at least one inclinometer is preferably selected from the group consisting of spirit level inclinometers, gyration inclinometers, and inertial inclinometers. Alternatively, or in addition, an inclinometer with a movable body having a position indicative of the orientation of the gravity vector may be used.

The imaging system may be configured to prepare a corrected image, which is corrected for the presence of the gravity induced image error. In this case, the system further comprises a processor to prepare the corrected image by relating the gravity induced deformation and the gravity induced image error.

Another embodiment of the present invention relates to a system for preparing a reduced error image from image data obtained using an imager. A reduced error image is an image that has been corrected for the presence of a gravity induced image error. The system comprises a processor to receive the image data and position data indicative of a gravity induced deformation of the imager. The processor is configured to prepare a reduced error image from the image data by correcting an image error associated with the gravity induced deformation of the imager. The reduced error image is preferably essentially free of the error associated with the gravity induced deformation of the imager.

Yet another embodiment of the invention relates to a method for obtaining an image, which is correctable for the presence of a gravity induced image error. The method comprises imaging an object with an imager to obtain an image of the object and obtaining position data indicative of a gravity-induced deformation of the imager. The method may comprise the further step of preparing an image corrected for the presence of the gravity induced image error by relating the gravity induced deformation and the gravity induced image error.

The step of obtaining the position data may include determining a respective position of at least three markers each having a known spatial relationship with respect to the imager.

Another embodiment of the present invention relates to a method for preparing a reduced error image of an object. The method comprises providing image data of the object, wherein the image data was obtained using an imager, and providing position data indicative of a gravity induced deformation of the imager. The image data is preferably in electronic format, such as a digitized image. The position data is used to prepare a reduced error image from the image data by correcting an image error associated with the gravity induced deformation of the imager.

Another embodiment of the present invention relates to a device for detecting the position and orientation of an imager, which is preferably provided with at least three non-collinear markers, within at least one three-dimensional coordinate system. The device includes a position measurement device for locating the markers within the coordinate system and a computer for determining the position and orientation of the body based upon position data received from the position sensor. The position measurement device preferably includes at least two light sensitive elements having a respective optical axis. The optical axes intersect at a point displaced from the position measurement device. The device also includes a gravity vector determination device, which provides gravity vector data indicative of the direction of the gravity vector within the coordinate system.

The gravity vector detection device comprises at least one inclinometer, which is fixed with respect to the position measurement device. A preferred embodiment includes two inclinometers each having a respective axis. The respective axes are angularly offset, such as perpendicularly, to one another. The inclinometers can include, for example, spirit level inclinometers, gyration inclinometers having a space-based angular momentum vector, and inertial inclinometers.

In one embodiment, the inclinometer comprises a body, which includes at least two markers displaced from one another by a distance. The body is preferably free to assume a spatial position indicative of the alignment of the body with respect to the gravity vector. The position measurement device determines the body's spatial position. The computer is configured to determine the direction of the gravity vector based upon the position of the body.

The body may be suspended, such as by a thread, wire, or chain. Joints, which allow the body to move, such as Cardon joints or ball and socket joints, may also be used. The body may also be embedded within a flexible material, such as an elastomer, for example, silicone or foamed silicone rubber.

Movement of the body, such as movement tending to bring the body into alignment with the gravity vector may be damped, such as by shock-absorption. For example, the body may be contacted with a liquid, damped by mechanical means, such as springs, or damped by electromagnetic means. The shock absorption may be provided by friction or pneumatic shock absorbers.

Yet another embodiment of the invention relates to a method for preparing corrected image, such as a corrected x-ray image, from images including gravity induced errors. Gravity induced errors may arise because of, for example, mechanical deformations of an imager used to obtain the images. For example, gravity induced deformations may introduce errors into images obtained using x-ray apparatus comprising an x-ray source and a receiver. A example of a image is an x-ray image, such as an x-ray photograph, which is preferably digitized and stored electronically.

The method comprises obtaining gravity vector data indicative of the direction of the gravity vector within a three-dimensional coordinate system. Imager position data indicative of the position and orientation of the imager within the coordinate system are obtained, preferably by using a position measurement device in communication with a computer. The corrected image is prepared based upon the position and orientation of the imager with respect to the gravity vector.

The corrected image is prepared without placing a calibration instrument between the source and receiver of the imager, which eliminates errors caused by such instruments. In addition, the influences of gravity and of the Earth's magnetic field on the x-ray photographs may also be determined and the image corrected for either or both gravity or magnetic field-induced errors.

In one embodiment of an imaging system of the invention, the system comprises a position measurement device having at least two optoelectronic cameras, which are preferably equipped with CCD chips (charge-coupled device chips). The position measurement system is configured to determine the positions of markers, preferably infrared light-emitting diodes (IREDs), within a sensor based coordinate system. The markers have a known spatial relationship to an imager, which allows the position and orientation of the imager to be determined within the sensor based coordinate system.

The system further includes a gravity vector determination device for determination of a direction of a local gravity vector. The gravity vector determination device includes a first inclinometer defining an x-axis of a gravity-based, three-dimensional coordinate system, a second inclinometer defining a y-axis of the gravity-based, three-dimensional coordinate system, and a computer equipped with software permitting a three-dimensional, real-time display in a numeric or graphic form.

The inclinometer axes form a plane extending perpendicularly to a local gravity vector thereby forming a three-dimensional, gravity-based coordinate system. By means of an electronic transmission of the signals emitted by the inclinometers to the computer, it is possible to determine a deviation in parallelism between one axis of the sensor-based coordinate system and the corresponding axis of the gravity-based coordinate system, and, consequently, to determine the rotation, if any, of the sensor-based coordinate system relative to the gravity-based coordinate system. The computer is configured to perform a coordinate transformation between the sensor-based coordinate system and the space-based or gravity-based coordinate system. Based on the coordinate transformation, the position and orientation of the imager can be determined with respect to the local gravity vector.

Another embodiment of the present invention relates to a method for obtaining an image of an object. The method includes obtaining an image of the object using an imager. Position data indicative of the position and orientation of the imager with respect to the direction of the local gravity vector within a three-dimensional coordinate system are obtained. The position data preferably include gravity vector data indicative of the direction of the local gravity vector within the three-dimensional coordinate system and imager position data indicative of the position of the imager within the three dimensional coordinate system. The position data may be stored, such as in a computer memory, for processing. A corrected image is prepared from image based on the position data. The corrected image is preferably essentially free of error, such as a distortion, caused by gravity induced mechanical deformations of the imager.

In a preferred embodiment, the method comprises determining the direction of a normal extending perpendicular to the image with the three dimensional coordinate system based upon the imager position data. The normal extends between a source and receiver of the imager. A second corrected image is prepared by correcting the image for errors caused by deviation of the normal from the direction of the Earth's local magnetic field. The image is preferably an x-ray photograph generated by the receiver on a magneto-optical basis. Errors of the magneto-optical photograph caused by optical deformations occurring in the receiver may be corrected.

BRIEF DESCRIPTION OF THE DRAWINGS

The present invention is described below in reference to the drawings in which.

DETAILED DESCRIPTION OF THE PREFERRED EMBODIMENT

Figure 1:
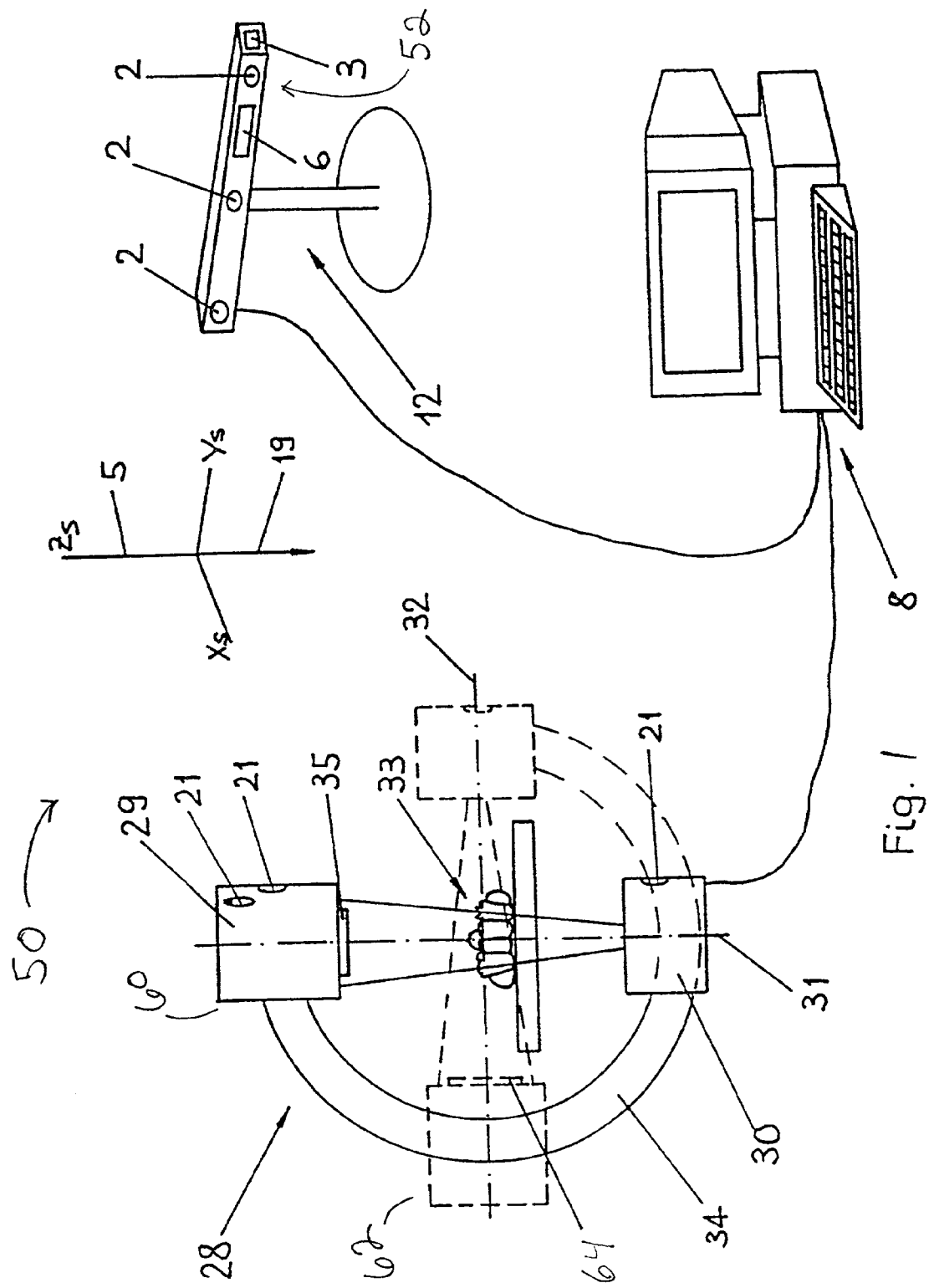
FIG. 1 shows an imaging device according to the invention.

Referring to FIG. 1, an imaging system 50 includes an imager 28, which is configured to obtain one or more images of an object, such as a human 33 or other animal.

The images may include gravity induced errors, such as image distortions caused by gravity induced deformations of the imager, including mechanical deformations in the shape or position of the imager. According to the present invention, the gravity induced errors are correctable upon obtaining position data indicative of the position and orientation of the imager with respect to a gravity vector 19 local to the imager. The position data may include imager position data indicative of the position and orientation of imager 28 and gravity vector data indicative of the direction of gravity vector 19. A position measurement device 12 provides the imager position data and a gravity vector determination device 52, which may be integral with position measurement device 12, provides the in-situ gravity vector data. A computer 8 receives image data from imager 28 and the position data. Computer 8 prepares corrected image data from the image data based upon the position data.

Imager 28 includes a source 30 and a receiver 29, which are preferably movable between a plurality of positions, such as between first and second positions 60, 62, and configured to obtain an image of the object from each of the plurality of positions. For example, object images, which are preferably formed parallel to image planes 35, 64, may be obtained from an anterior-posterior direction and a lateral-medial direction, such that respective image axes 31, 32, which are normal to respective image planes 35, 64 extend approximately vertically or horizontally, depending on the position of imager 28. Mechanical deformations of the imager differ depending on whether the imager is oriented horizontally or vertically.

Imager 28 may be an x-ray imager configured to obtain at least one x-ray image of the object. A rotatable or swivel-mounted x-ray imager configured to obtain x-ray images from different orientations is preferred. Source 30 may be an x-ray source and receiver 29 an x-ray receiver, which preferably cooperate to generate an x-ray image on a magneto-optical basis.

Imager 28 includes markers 21 to allow determination of a position and orientation of imager 28 by position measurement device 12. Markers 21 preferably emit energy. For example, markers 21 may comprise light sources, such as light emitting diodes, infrared light emitting diodes and reflectors configured to reflect light emitted from a light source displaced from the markers. Acoustic energy sources, such as acoustic transmitters, may be used. The markers may comprise magnetic field generating elements, such as electromagnetic coils.

Figure 2:
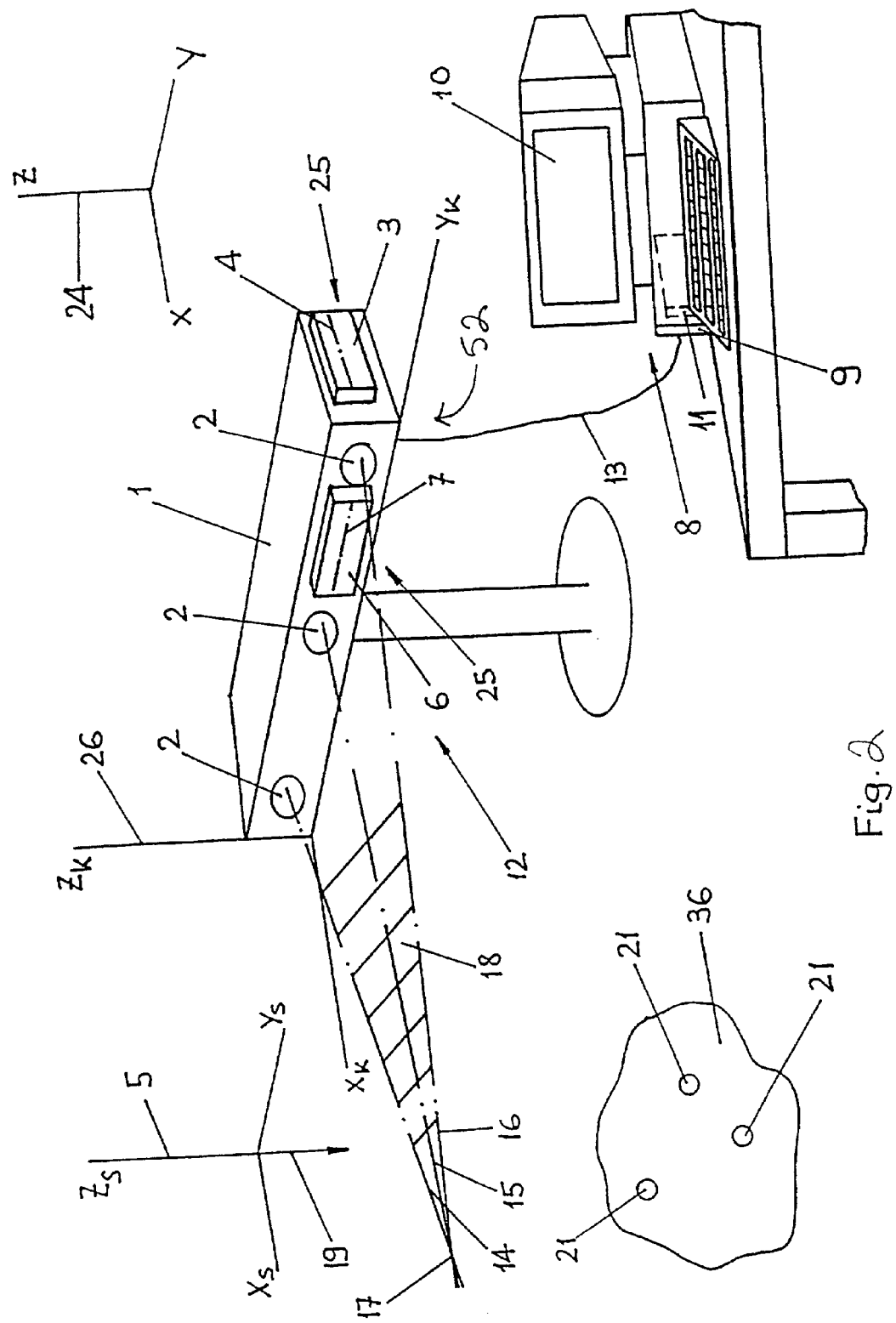
FIG. 2 shows a position measurement device of the imaging system of FIG. 1.

Referring to FIG. 2, position measurement device 12 includes receivers to receive energy emitted by markers 21. In the embodiment of FIG. 2, markers 21 are light emitting diodes and each of the receivers is an optoelectronic camera 2, which preferably include linear charge coupled device (CCD) chips to detect light from markers 21. An example of a position measurement device comprising camera elements is the model OPTOTRAK 3020 System available from Northern Digital, Waterloo, Ontario. Receivers of alternative position measurement devices include other light sensitive elements, such as photodiodes; acoustic receivers, such as microphones; and magnetic field sensitive receivers such as Hall effect components. It should be understood that markers 21 may be configured as receivers rather than emitters and that position measurement device 12 may include emitters rather than receivers.

Position measurement device 12 outputs imager position data indicative of a position of markers 21. Because the position of markers 12 is known with respect to imager 28, the position data are also indicative of the position and orientation of imager 28. Computer 8 receives and processes the imager position data. Computer 8 is programmed, such as with software, to display the data received thereby. Data are preferably displayed real-time, such as in numeric form or graphically in three-dimensions on a display 10. To facilitate the reception and processing of the image data, system 50 includes a system control unit 9, which is preferably integral with the computer 8, cables 13, which connect computer 8 and position measurement device 12, and an interface card 11.

Gravity vector determination device 52 includes first and second inclinometers 3, 6, which are preferably fixed with respect to position measurement device 12. The inclinometers are configured to determine deviations from the gravity vector 19. A horizontal axis 4 of inclinometer 3 defines an x-axis of a gravity-based, three-dimensional coordinate system 5. A horizontal axis 7 of second inclinometer 6 extends at an angle, preferably perpendicularly, to horizontal axis 4 and forms the y-axis of coordinate system 5. An axis $X_K$ of a sensor-based, three-dimensional coordinate system 26 is aligned preferably parallel to the horizontal axis 4 of first inclinometer 3 and an axis $Y_K$ of coordinate system 26 is aligned preferably parallel to horizontal axis 7 of second inclinometer 6. Optical axes 14-16 of cameras 2 intersect at a point 17 and define a plane 18, which extends at an angle, preferably perpendicularly, to gravity vector 19.

Imaging system 50 determines the presence of angular deviation between one or more of the sensor-based coordinate axes $X_K$, $Y_K$ and the corresponding axis 4, 7 of the respective inclinometer 3, 6. The angular deviation is preferably indicative of the angular deviation (rotation) of the sensor-based coordinate system 26 relative to the gravity-based coordinate system 5. Computer 8 is configured to perform a coordinate transformation between the sensor-based and gravity-based coordinate systems. Therefore, the image position data and gravity vector data allow the position and orientation of imager 28 to be determined with respect to the local gravity vector. Deformations of imager 28, which may depend on the orientation of imager 28 with respect to the local gravity vector, may be determined based on the position data, which may include image position data, gravity vector data, or a combination thereof. For example, the imager position data may be indicative of a deviation of image planes 35, 64 from a respective desired orientation of normal axes 31, 32. Such deviations may cause image errors of images obtained by imager 28. Computer 8 is configured to prepare a corrected image based on the position data.

Inclinometers useful with the present invention include, spirit level inclinometers including a liquid with associated gas bubble, gyration inclinometers, and inertial inclinometers. Inclinometers including magnetic elements analogous to a compass may also be used. Gyration and inertial inclinometers are preferably calibrated with respect to an initial orientation with respect to the gravity vector.

Figure 3:
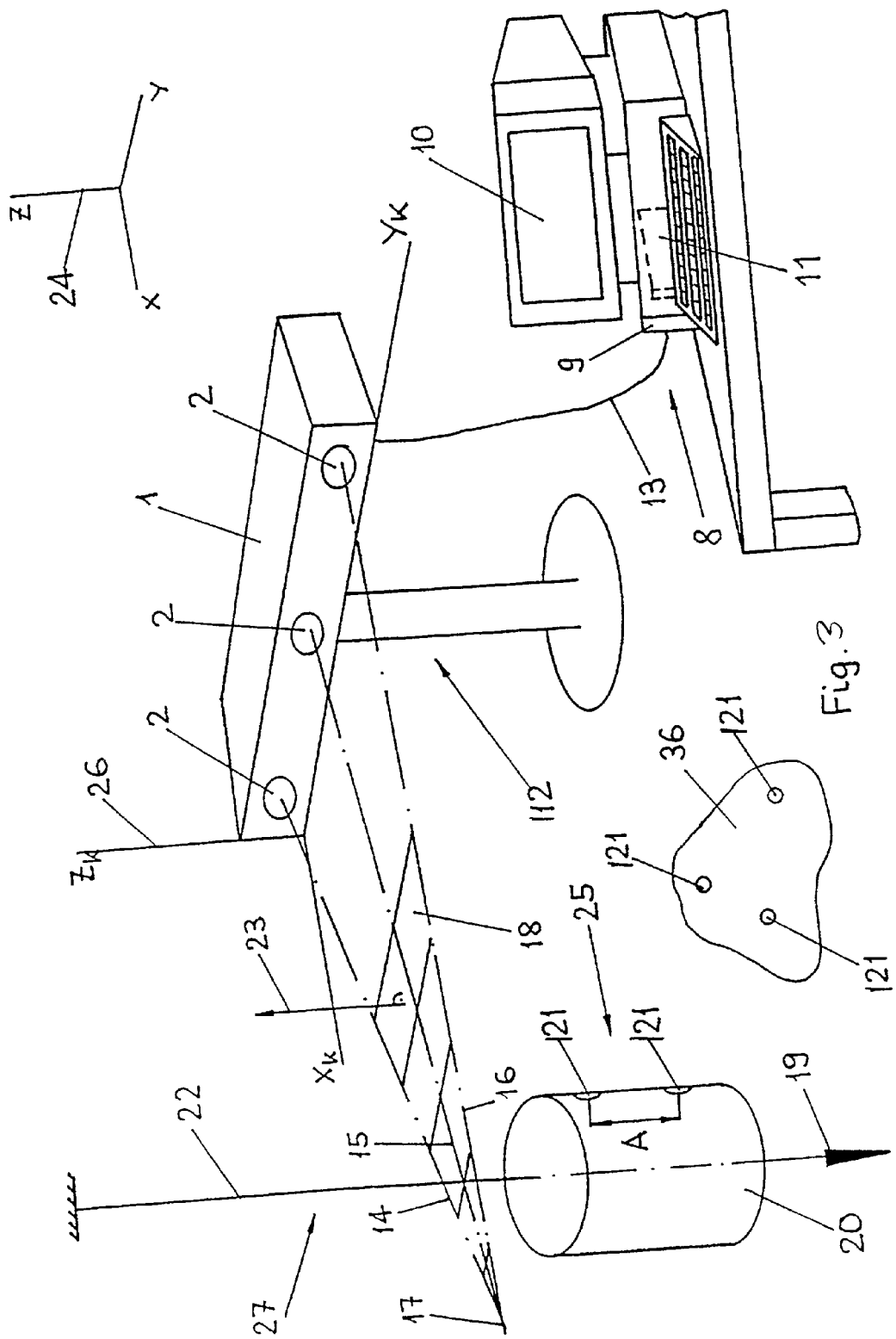
FIG. 3 shows a second position measurement device according to the invention.

Referring to FIG. 3, a position measurement device 100 differs from position measurement device 12 in that determination of the direction of the gravity vector 19 comprises determining the alignment of a body 20 with respect to the gravity vector. Body 20 is preferably movable such that it tends to assume a position indicative of the direction of the local gravity vector. For example, body 20 may be suspended, such as by a thin thread or wire 22. Body 20 is equipped with at least two markers 121 displaced from one another by a distance A. Markers 121 are preferably configured to emit energy, such as light, as discussed above for markers 21.

Energy emitted by the markers 121 is detected by cameras 2 of position detector 112, which provides body position data indicative of the positions of the markers 121 in space. The spatial positions of body 20 and, therefore, markers 121 are influenced by the direction of gravity vector 19. Computer 8 is configured to determine the direction of gravity vector 19 based upon the body position data. In case of a deviation in parallelism between the sensor-based normal 23 extending perpendicularly to the plane 18 formed by the optical axes 14, 15, 16 of the cameras 2 and the gravity vector 19, the deviation is detected by position measurement device 112. The rotation of the sensor-based coordinate system 26 relative to the gravity-based coordinate system 5 is determined by computer 8 by processing of the signals corresponding to the deviation detected by the position measurement device 112.

The present invention also provides a method for obtaining an image, which is correctable for the presence of a gravity induced image error. An object is imaged, such as with imager 28, to obtain an image of the object. A gravity induced deformation of the imager is determined, such as by using a position measurement device of the invention. For example, the position and orientation of an x-ray source 30 and/or the receiver 29 may be determined by measuring positions of markers 21 having a known relationship to the x-ray source 30 and/or the receiver 29. Determining the position of respective sets of markers fixed with respect to the source and receiver, respectively, allows deviations in alignment between the source and receiver to be determined from the imager position data.

The direction (orientation) of the gravity vector 19 is determined within a three-dimensional coordinate system 5, 24, 26 using a position measurement device and computer. For example, a space-based coordinate system 24 may be determined by measuring the positions of at least three non-collinear markers 21 having a fixed position in space, while the determination of the gravity-based, three-dimensional coordinate system 5, which is equally space-based, may be realised by measuring the positions of axes 4, 7 of inclinometers 3, 6 and their point of intersection. Alternatively, the gravity based coordinate system may be determined by measuring the positions of at least three markers 21 associated with body 20.

The position and orientation of x-ray source 30 and/or the receiver 29 are determined within coordinate system 5, 24, 26 using a position measurement device such as by measuring the positions of the markers 21 fixed on the source 30 and/or the receiver 29.

Distortions of images obtained by the imager, due to gravity-induced, mechanical deformations of the imager 28, may be determined using computer 8. The distorted image may be corrected to provide a reduced error image using the computer 8.

The direction of the image plane normal 31, 32 extending perpendicularly to the image within coordinate system 5, 24, 26 may be determined from the position and orientation of the receiver 29. Image errors generated by the receiver 29 arising from the deviation of the respective normal 31, 32 of said photograph from the direction of the Earth's local magnetic field may be determined by means of the computer 8. The image may be corrected to provide a reduced error image corrected for the presence of magnetic field induced errors. Magnetic field induced errors may be present in, for example, x-ray photographs obtained on a magneto-optical basis. Distortions of the magneto-optical x-ray photograph caused by optical deformations occurring in receiver 29, which distortions are particularly affected, among other things, by the vertical or horizontal orientation of the x-ray apparatus 28, may be corrected using computer 8.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. An imaging system for obtaining a reduced error image that is correctable for the presence of a gravity induced image error, said imaging system comprising:
    an imager to obtain an image of an object, the objected being in a suspended state;
    at least two markers displaced from one another by a distance attached to the object;
    a position measurement device providing object position data indicative of positions of the markers; and
    a computer configured to determine a direction of a gravity vector based on the object position data,
    wherein deviation of parallelism between the gravity vector and a sensor-based normal is determined by the position measurement device,
    wherein the imager is rotated to eliminate the deviation of parallelism between the gravity vector and a sensor-based normal of a sensor-based coordinate system, and
    wherein the reduced error image of the objected is taken by the imager.

2. An imaging system according to claim 1, wherein the imager includes multiple optical axes intersecting at a point to define a plane.

3. An imaging system according to claim 2, wherein the sensor-based normal is perpendicular to the plane.

4. An imaging system according to claim 1, wherein the markers are energy emitting markers having a known spatial relationship with respect to the imager.

5. An imaging system according to claim 1, wherein the position measurement device comprises receivers to determine the positions of the markers.

6. An imaging system according to claim 1, wherein the object is suspended by a wire.

7. An imaging system according to claim 3, wherein an x-axis of a gravity-based three-dimensional coordinate system is aligned parallel with a horizontal axis of the imager.

8. An imaging system according to claim 7, wherein an x-axis of a sensor-based three dimensional coordinate system is parallel to the plane.

9. An imaging system according to claim 8, wherein the deviation of parallelism between the gravity vector and the sensor-based normal is based on an angular deviation of the sensor-based coordinate system relative to the gravity-based coordinate system.

10. An imaging system according to claim 9, wherein the reduced error image is obtained by rotation of the sensor-based coordinate system relative to the gravity-based coordinate system as determined by the computer processing signals corresponding to the deviation of parallelism detected by the position measurement device.

11. An imaging system according to claim 1, wherein the imager is an x-ray apparatus and the image is an x-ray image of an animal.

12. A method imaging system for obtaining a reduced error image that is correctable for the presence of a gravity induced image error, said method comprising the steps of:
attaching at least two markers displaced from one another by a distance onto an object to be imaged by an imager;
suspending the objected such that the object is movable;
obtaining object position data indicative of positions of the markers by a position measurement device;
determining a direction of a gravity vector based on the object position data;
determining a deviation of parallelism between the gravity vector and a sensor-based normal of a sensor-based coordinate system;
rotating the imager to eliminate the deviation of parallelism between the gravity vector and a sensor-based normal of a sensor-based coordinate system; and
taking the reduced error image of the objected by the imager.

13. A method according to claim 12, wherein the imager includes multiple optical axes intersecting at a point to define a plane.

14. A method according to claim 13, wherein the sensor-based normal is perpendicular to the plane.

15. A method according to claim 12, wherein the markers are energy emitting markers having a known spatial relationship with respect to the imager.

16. A method according to claim 12, wherein the position measurement device comprises receivers to determine the positions of the markers.

17. A method according to claim 12, wherein the object is suspended by a wire.

18. A method according to claim 14, wherein an x-axis of a gravity-based three-dimensional coordinate system is aligned parallel with a horizontal axis of the imager.

19. A method according to claim 18, wherein an x-axis of the sensor-based three dimensional coordinate system is parallel to the plane.

20. A method according to claim 19, wherein the deviation of parallelism between the gravity vector and the sensor-based normal is based on an angular deviation of the sensor-based coordinate system relative to the gravity-based coordinate system.

21. A method according to claim 20, wherein a reduced error image is obtained by rotation of the sensor-based coordinate system relative to the gravity-based coordinate system as determined by the computer processing signals corresponding to the deviation of parallelism detected by the position measurement device.

22. A method according to claim 12, wherein the imager is an x-ray apparatus and the image is an x-ray image of an animal.

* * * * *